United States Patent [19]

Burlage et al.

[11] Patent Number: 4,841,961
[45] Date of Patent: Jun. 27, 1989

[54] PATIENT RESTRAINING DEVICE AND TEMPORARY TRANSPORT

[76] Inventors: Bonnie Burlage, Box 473; Donna Steinmann, Rte. 2; Margaret Reiman, Box 515, all of Ashton, Id. 83420

[21] Appl. No.: 931,555

[22] Filed: Nov. 17, 1986

[51] Int. Cl.⁴ .......................... A61F 5/37; A61G 1/00
[52] U.S. Cl. .......................................... 128/876; 5/82 R
[58] Field of Search ............... 128/78, 87 R, 134, 133; 5/82 R, 82 B; 2/333; 24/302

[56] References Cited

U.S. PATENT DOCUMENTS

| | | | |
|---|---|---|---|
| 3,321,247 | 5/1967 | Dillender | 297/473 X |
| 3,620,211 | 11/1971 | Goodell et al. | 128/78 X |
| 3,889,668 | 6/1975 | Ochs et al. | 128/134 |
| 3,933,154 | 1/1976 | Cabansag | 128/134 |
| 4,050,737 | 9/1977 | Jordan | 128/134 X |
| 4,205,670 | 6/1980 | Owens | 128/134 |
| 4,299,211 | 11/1981 | Doynow | 128/134 X |
| 4,422,454 | 12/1983 | English | 128/134 |

Primary Examiner—Richard T. Stouffer
Attorney, Agent, or Firm—Hopkins, French, Crockett Springer & Hoopes

[57] ABSTRACT

A patient restraint device adapted to secure a victim to a temporary transport apparatus, such as a backboard or a gurney. The device incorporates one or more pairs of moveable strap members which can be adjusted depending upon the size of the victim, location of wounds and location of securing points on the backboard or gurney. The device is especially suited for construction in small (infant), medium (adult) or large (for extremely obese or extremely tall victims) sizes. The device can be color-coded so that it can be applied to the victim in a "right side up" arrangement the first time.

3 Claims, 2 Drawing Sheets

PATIENT RESTRAINING DEVICE AND TEMPORARY TRANSPORT

BACKGROUND OF THE INVENTION

This invention relates to an apparatus for use by emergency medical personnel to secure a patient or accident victim to a temporary transport means, such as a backboard or a gurney. More particularly, it relates to a restraint device which is particularly adaptable to secure accident victims of varying sizes to backboards at the scene of an accident for transport to a medical facility.

As a result of the Korean and Vietnam wars, the quality of emergency medical care in the field has dramatically increased survival chances for persons injured in, e.g., automobile accidents. Ambulance, fire department and hospital personnel responding to such calls very often find the need to transport the injured victim some distance between the injury site and the ambulance or other transport vehicle. For this purpose, rigid backboards or wheeled gurneys are typically utilized. The patient must be affixed to the temporary transport means in order to avoid rolling off the backboard or gurney and further exacerbating the injuries.

For years such temporary transport means were provided with a number of straps permanently affixed to their sides, most typically three straps: one at the shoulders, one at the abdomen, and a third at the knees. In many instances, it was found that the placement of these permanent straps was inconvenient, if not hazardous, in that the patient may be unusually small (an infant), large (either in height or girth), or have a wound or injury which should not be compressed by the fixed-in-place strap. U.S. Pat. No. 4,151,842 discloses a body splint/litter device having a plurality of fixed straps, located at the head, shoulders, abdomen and knees of the patient.

Of course, not all temporary transport means are/or were provided with such straps. U.S. Pat. No. 3,889,668 discloses an emergency medical harness which permits an accident victim to be secured to a half-backboard, as at the site of an automobile accident. The device comprises a plurality of straps 12, 14 and 16 spaced laterally from one another, but secured together by webs 18–22 at points 30. In this manner, a net-like upper torso restraining device was created. The device is especially intended for use with a rigid backboard having a plurality of slots 40–45 through which the straps 12–16 were threaded. Shoulder 50, 51 and hip 62, 63 straps were also provided.

While the device of U.S. Pat. No. 3,889,668 certainly functions adequately for a portion of the intended patients, a problem arises when the backboard upon which the patient is to be secured does not have slots in the precise position where the straps of the device are located. Because the straps are secured a fixed distance from one another by the webs, they cannot be moved an appreciable distance to a non-aligning slot. There are a number of different manufacturers of backboards and gurneys, and there is not a recognized standard for the placement of hand-holds or other apertures into which the straps of such a harness may be affixed. Additionally, if the patient has suffered a severe abdominal wound, it may be advisable to forego use of the device to avoid further injury to the patient.

Because every second in such emergency situations is critical to increasing the survival chances of the patient, it is necessary that some indicia be provided to indicate when the harness is in a "right side up" position, and therefore can be readily affixed to the temporary transport means. If, as disclosed in the '668 patent, Velcro ® brand fasteners are used to affix the harness to the backboard, the harness can only be properly affixed in the right side up position. If the harness is placed on the patient "wrong side up" the hook-and-pile regions of the strap will not mate without first twisting the strap. herefore, the device must be removed, turned over, and rethreaded, through the slots.

Therefore, there is a need for a patient restraint device which is adjustable to accommodate differing patients as well as differing transport means. There is also a need for a patient restraint device which is color coded so that it will be immediately apparent which side of the restraint device is "right side up".

Therefore, a general object of the present invention is to provide a new and improved patient restraint device which is adaptable to various size patients, various injuries and differing brands of temporary transport means.

A specific object of the present invention is to provide a new and improved patient restraint device having moveable straps securing the patient to the temporary transport means, and a device which is color coded to insure proper placement of the device on the patient the first time.

SUMMARY OF THE INVENTION

A patient restraint device constructed in accordance with the present invention includes a first ventral strap member adapted to be positioned longitudinally along the body of a supine or prone patient; a pair of second strap members obliquely oriented to the ventral strap member and adapted to secure the shoulders of the patient; one or more pairs of third strap members disposed on either side of the ventral strap member, at least one of which is moveably affixed to the ventral strap member so that it may be moved longitudinally along the ventral strap member; and latch means on each of the second and third strap members to secure the device to a temporary transport means, with a patient immobilized therebetween. More particularly, the first, second and third strap members are color-coded to insure proper placement of the device on the patient in a "right side up" position. Also, when the device is folded into a compact unit for storage, a storage means is provided to secure the device in a small and manageable bundle.

DETAILED DESCRIPTION OF THE INVENTION

Many persons in emergency situations, such as motor vehicle accidents, falls from ladders or trees, or slip-and-fall incidents, require immobilization of all or a portion of their bodies during transport to a medical facility. Additionally, it can be advantageous when transporting any seriously ill or unconscious person, whether or not the result of an accident, to secure the person's body to a temporary transport apparatus (such as a backboard or a gurney) which can likewise be secured within the transport vehicle. In this manner, the backboard or gurney can be used to transport the victim between the accident site and the transport vehicle, then secured in the vehicle and later transported from the vehicle to the medical facility, without fear of the body falling off the backboard or gurney, and thereby further injuring the individual.

The invention disclosed herein is a highly effective means of securing an individual in need of transport to and from an ambulance, and transport from an accident site to a medical facility in such ambulance. Of course, while the invention described herein is set in the context of transport within an ambulance, it is equally susceptible of advantageous use in a helicopter, airplane, or any other similar transport vehicle. It should also be equally apparent that transport on a gurney, backboard, etc., can be within a medical facility, as for instance between a patient's room and an operating room, as well as to and from an ambulance.

Figure 1:
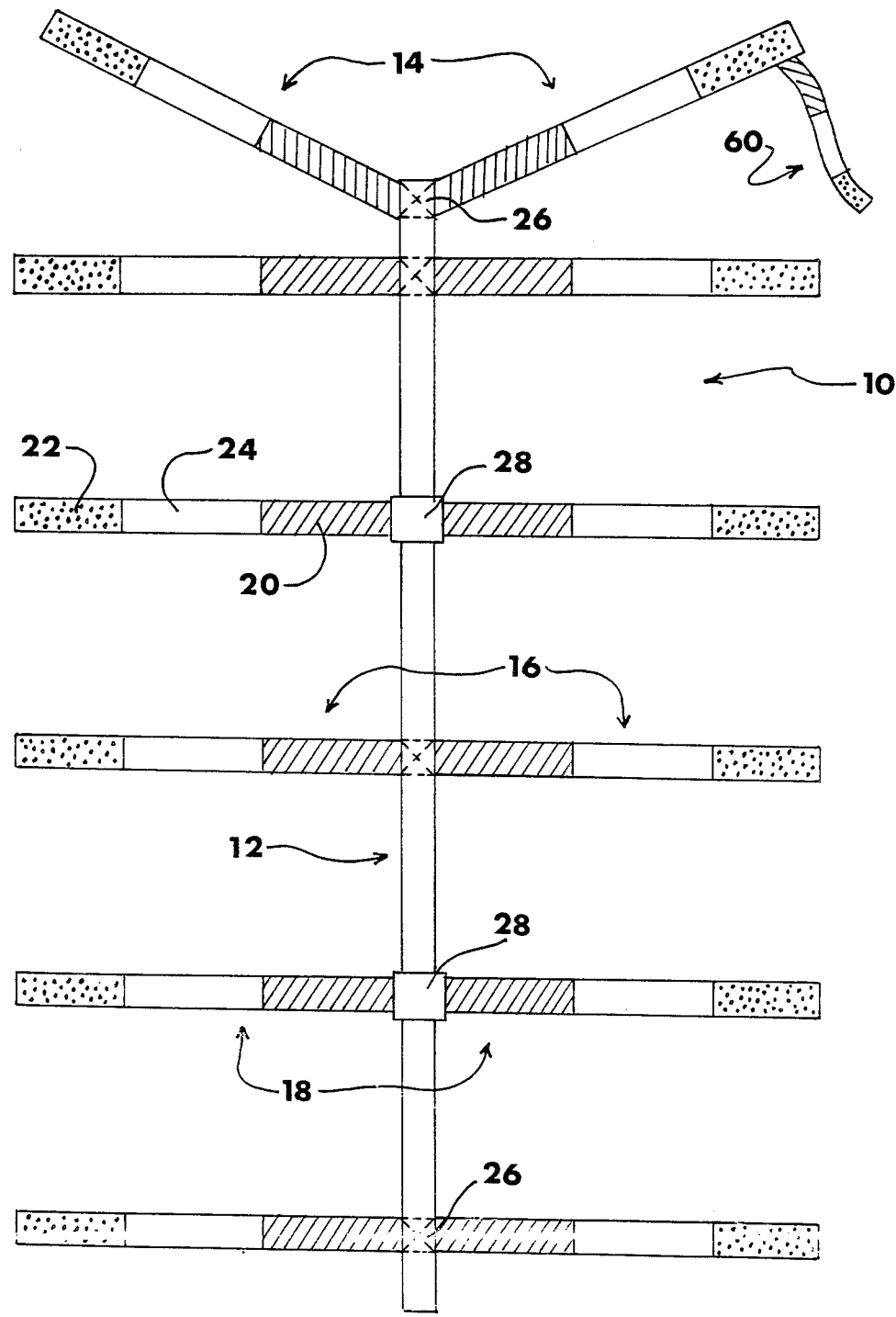
FIG. 1 is a front-elevational view of the patient restraint device of the present invention.

FIG. 1 illustrates the present invention in plan view. The invention, generally designated at 10, comprises a ventral strap member, 12, which is adapted to overlie, from head to foot, the body of the patient. Generally speaking, there is a pair of second strap members, generally indicated at 14, one or more pairs of third strap members, generally indicated at 16 which are adapted to be affixed to the first ventral strap member 12, and optionally, one or more pairs of fourth strap members, generally indicated at 18, which also are affixed to the first ventral strap member 12. Each of the second, third and fourth strap members is provided with latch means by which the device 10 can be secured to a temporary transport device. While this latch means can take the form of any well known latch means, such as a belt buckle-type device, a spring activated clamp-type buckle, a friction activated cam-type buckle, etc., the applicant has found that the easiest and quickest latch means is the hook-and-pile Velcro ® brand attaching device. In this embodiment, each half of the second, third, and fourth strap members is provided with a section of hook 20, and pile 22, such that when the individual halves of each strap member is folded upon itself, the hook-and-pile sections engage one another. Between the hook 20 and pile 22 sections can be a section of the strap member 24, devoid of either the hook 20 or the pile 22 means. The section 24 is that section which is in contact with the temporary transport device upon which the patient is carried.

In a preferred embodiment, the second and third strap members, 14 and 16 respectively, are permanently affixed to the first strap member, 12, as at their points of intersection, 26. Conversely, the applicant has found that it is advantageous to provide one or more fourth strap members 18, which are not permanently affixed to the first strap member 12, but are moveably or slideably affixed thereto, as by a sleeve 28. In this manner, the fourth strap members are adjustable along the first strap member 12.

Figure 2:
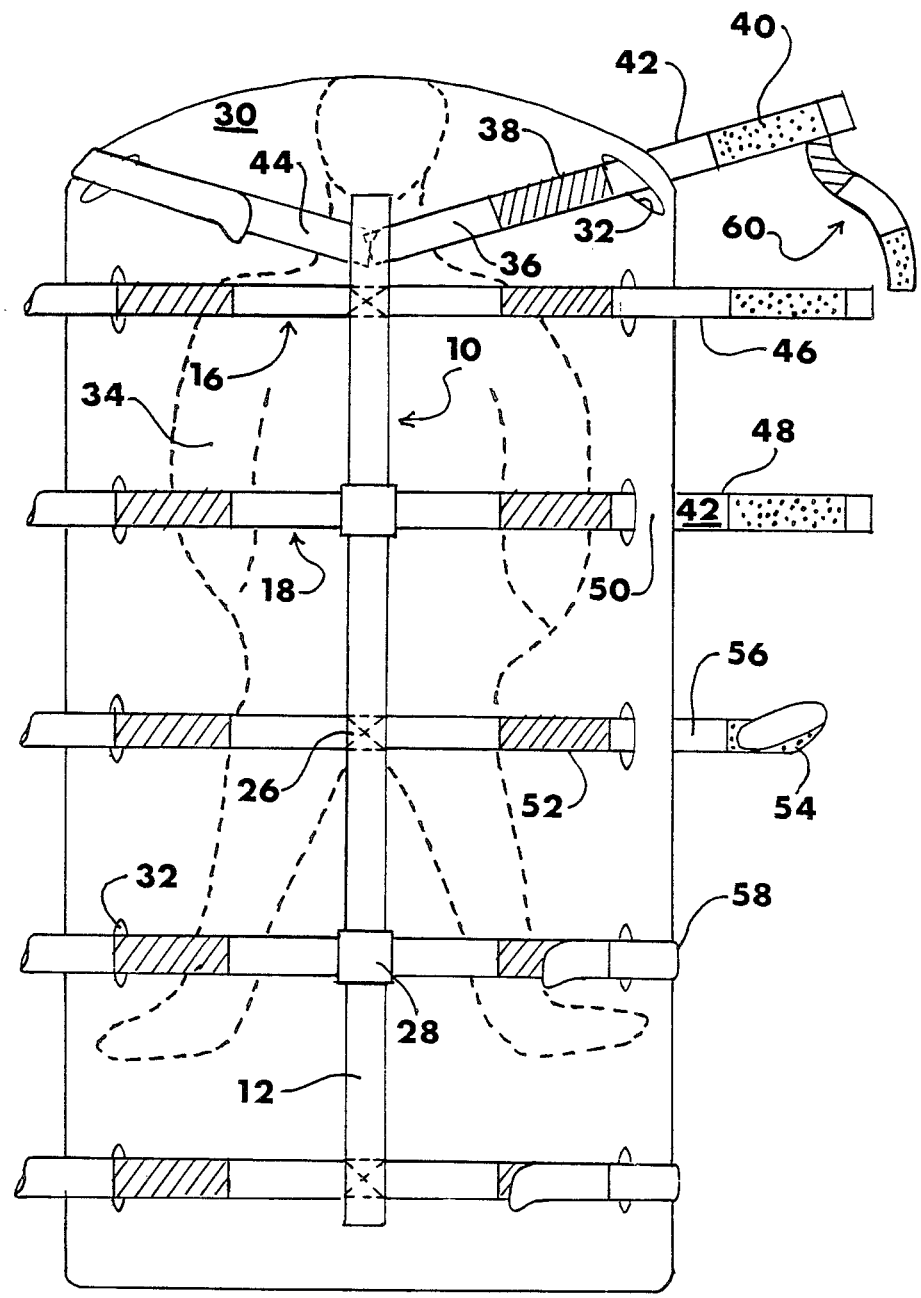
FIG. 2 is a top-elevational view of the patient restraint device of the present invention as applied to a victim on a backboard.

Turning now to FIG. 2, there is illustrated a temporary transport device 30, in the form of a rigid backboard having a plurality of apertures 32, about the periphery thereof which traditionally serve as hand-holds for the medical personnel transporting an injured patient. These apertures 32, have also served as hold-down points for whatever sort of individual straps may have been used to secure the patient to the device 30 (if any). It is to be understood that while the present invention is disclosed in FIG. 2 in cooperation with a backboard, any other conventional temporary transport device (such as a gurney) which has lateral means about which the second, third or fourth strap members may be affixed, is equally acceptable.

As shown in FIG. 2, there is a patient, indicated at 34, who has been placed upon the transport device 30 for transport from an accident location to an ambulance, for transport within the ambulance, and transport from the ambulance to the medical facility. In many types of injuries, especially neck, back or spinal cord injuries, it is imperative that the injured party be maintained in as immobile a condition as possible in order to avoid further exacerbation of the injury. Likewise, an individual with an injury of any sort whatsoever which will require transportation on such a temporary transport device must be secured to the device 30, so that he/she will not fall or roll off the device during transport to the ambulance, or once in the ambulance, while in transit to the medical facility. The present invention is uniquely suited to fulfill all these requirements.

Once a patient is placed upon the temporary transport device 30 the present invention 10 may be unfurled from its stored position (as hereinafter described) and placed upon the patient's body. While the patient 34 is indicated in FIG. 2 to be in a supine position, it is to be understood that the present invention is equally adapted to secure a patient to a temporary transport device who must be transported in a prone position.

The first ventral strap member 12 is aligned on the longitudinal axis of the patient's body from just below the chin toward the feet. The pair of second strap members 14, affixed to the first ventral strap member at equivalent oblique angles, are laid across the patient's shoulders and affixed through apertures 32 adjacent the patient's head. As indicated, one of the pair of second strap members 36 is shown in an extended, unattached position through its cooperating aperture 32. The strap 36 is provided with a hook 38 and pile 40 region, as well as a barren region 42 which is intended to secure the strap 36 to transport device 30 at aperture 32. When directed through the apperture 32 and then back upon itself, the hook-and-pile cooperate to securely affix the strap, as indicated at 44, to the transport device 30.

Further strap members, aligned perpendicularly to the first ventral strap 12 may either be securely affixed thereto or slideably affixed thereto. Third strap members 16 can be securely affixed to the ventral strap 12 where they intersect, 26. Alternatively, fourth strap members 18 may be provided with a sleeve or collar 28 which permits the pair of strap members to be moved in either direction along the first ventral strap member 12. In this manner, while there may always be a need to secure the shoulders and upper body of a patient, the second strap members 14 and the upper-most third strap member 16 is sewn to the first ventral strap member 12, it may be advantageous to provide moveable fourth strap members 18 to accommodate patients of different size, to avoid placing a strap member upon an injured body part, or for other reasons. While FIG. 2 illustrates alternating third 16 and fourth 18 strap members, it should be apparent that the inventive device could be provided with any combination of such straps, from all affixed, to all moveable.

FIG. 2 illustrates the sequence of affixing the perpendicularly aligned third and fourth strap members to the temporary transport device 30. First, a strap 46 is extended fully across one-half of the patient's body. Next, the strap 48 is directed through apperture 32. While not absolutely necessary, it may be desirable that the barren space 42 in strap 48 bear against the lateral edge portion 50 of transport device 30. When the hook 52 and pile 54 regions of strap 56 are mated, the strap 58 is fully secured to the transport device 30 with the patient therebetween. Of course, all the straps are secured before moving the patient.

After use, the device 10 can be folded for storage. By laying the device flat, as in FIG. 1, and by sequentially placing the perpendicularly aligned strap members sequentially on top of one another from the bottom to the top, and then folding one side to the other, a relatively small bundle of straps is effected. A small storage strap 60 can be provided on one of the lateral straps so that when the device is fully folded, the storage strap 60 may be wrapped around the bundle to secure it in place. As with the other straps, the storage strap 60 may advantageously be provided with latch means, such as hook-and-pile Velcro ® brand fasteners, for easy engagement and disengagement.

Regardless of the type of latch means utilized, there is usually a more convenient "right side up" position in which to secure the latch. For instance, with the Velcro ® brand fasteners shown in FIG. 2 or with a conventional belt fastener, there is an "up" and a "down" side. Applicant has found that by color-coding the various straps, the medical personnel will always align the device 10 in the "up" position for quicker securing of the patient. For instance, if the first ventral strap member is a particular color, e.g., red, and the second third and fourth strap members are a different color, e.g., black, with the sleeve portion 28 matching that of the first ventral strap number 12, if the second, third and fourth strap members are initially secured on the bottom side of the first ventral strap member there will be a uniform red strip down the first ventral strap member 12. Conversely, on the backside of the device, the red color of the first ventral strap member 12 will be broken by the black of the second, third and fourth strap members, indicating that it is the underside and should be turned over for use with a patient.

The strap material may be any conventional material sufficiently strong to withstand the rigors of emergency medical care in the field. For instance, straps made of nylon webbing, canvas, silk, or any other non-stretchable material will suffice. It will be easily within the knowledge of one skilled in the art to choose the appropriate strap material, although for purposes of strength, workability, price and easy cleaning, applicant has found that 2 inch, tightly woven nylon webbing is sufficient.

It should be understood that size is not a determining feature of this invention. For that reason, the device may be provided in a large size for adults, a medium size for adolescents, and a small or pediatric size for infants. It is contemplated that in all other respects the invention would remain identical to that disclosed above.

The above description is merely representative of embodiments currently contemplated by applicants. Therefore, the invention is not intended to be limited thereby, but should be defined solely by the appended claims.

We claim:

1. In combination, a patient restraint device and a temporary transport means having apertures therein, said patient restraint device comprising:
   a. a single first ventral strap member adapted to be aligned along a longitudinal axis of a patient's body on the upper surface thereof from one end of said single first ventral strap member adapted to be positioned just below the chin of said patient to a second end of said strap member adapted to be adjacent the patient's feet when the patient is in a supine or prone position;
   b. a pair of second strap members obliquely oriented to said single first ventral strap member and permanently directly affixed solely thereto at the one end thereof adapted to be positioned below said chin;
   c. at least one pair of third strap members permanently secured solely to said single first ventral strap member and oriented perpendicularly thereto;
   d. at least one pair of fourth strap members having a sleeve intermediate the lateral ends thereof, said single first ventral strap member positioned through said sleeve such that said fourth strap members are slidably attached by said sleeves solely to the single first ventral strap member; and
   e. each of the second, third and fourth strap members having latch means thereon such that said strap members are directed through said apertures provided on the temporary transport means in order to securely affix the patient restraint device to the temporary transport means with said patient immobilized therebetween.

2. In combination, a patient restraint device and a temporary transport means having apertures therein, said patient restraint device comprising:
   a. a single first ventral strap member adapted to be aligned along a longitudinal axis of a patient's body on the upper surface thereof from one end of said single first ventral strap member adapted to be positioned just below the chin of said patient to a second end of said strap member adapted to be adjacent the the patient's feet when the patient is in a supine or prone position;
b. a pair of second strap members obliquely oriented to said single first ventral strap member and permanently directly affixed solely thereto at the one end thereof adapted to be positioned below said chin;
c. at least one pair of third strap members permanently secured solely to said single first ventral strap member and oriented perpendicularly thereto;
d. at least one pair of fourth strap members having a sleeve intermediate the lateral ends thereof, said single first ventral strap member positioned through said sleeve such that said fourth strap members are slidably attached by said sleeves solely to the single first ventral strap member;
e. each of the second, third and fourth strap members having latch means thereon such that said strap members are directed through said apertures provided on the temporary transport means in order to securely affix the patient restraint device to the temporary transport means with said patient immobilized therebetween; and
f. at least one of said second, third, or fourth strap members being provided with storage means comprising a fifth strap member, said fifth strap member being provided on one of the second, third or fourth strap members and being spaced apart from the first single ventral strap member and being adapted to be wrapped around the device when said device is folded upon itself for storage.

3. In combination, a patient restraint device and a temporary transport means having apertures therein, said patient restraint device comprising:
a. a single first ventral strap member adapted to be aligned along a longitudinal axis of a patient's body on the upper surface thereof from one end of said single first ventral strap member adapted to be positioned just below the chin of said patient to a second end of said strap member adapted to be adjacent the patient's feet when the patient is in a supine or prone position;
b. a pair of second strap members obliquely oriented to said single first ventral strap member and permanently directly affixed solely thereto at the one end thereof adapted to be positioned below said chin;
c. a plurality of pairs of additional strap members having a sleeve intermediate the lateral ends thereof, said single first ventral strap member positioned through said sleeves such that said additional strap members are oriented perpendicular to said single first ventral strap member and are slidably attached by said sleeves solely to the single first strap member; and
d. each of the second and additional strap members having latch means thereon such that said strap members are directed through said apertures provided on the temporary transport means in order to securely affix the patient restraint device to the temporary transport means with said patient immobilized therebetween.

* * * * *